US007267961B2

(12) United States Patent
Hu et al.

(10) Patent No.: US 7,267,961 B2
(45) Date of Patent: Sep. 11, 2007

(54) PEPTIDES FROM THE E7 PROTEIN OF HUMAN PAPILLOMA VIRUSES 16 AND 18 FOR DETECTING AND/OR DIAGNOSING CERVICAL AND OTHER HUMAN PAPILLOMA VIRUS ASSOCIATED CANCERS

(75) Inventors: Yao Xiong Hu, 234 Escuela Ave., #61, Mountain View, CA (US) 94040; Mark J. Rosenfeld, Draper, UT (US)

(73) Assignee: Yao Xiong Hu, Mountain View, CA (US)

( * ) Notice: Subject to any disclaimer, the term of this patent is extended or adjusted under 35 U.S.C. 154(b) by 394 days.

(21) Appl. No.: 10/995,902

(22) Filed: Nov. 23, 2004

(65) Prior Publication Data

US 2005/0221295 A1    Oct. 6, 2005

Related U.S. Application Data

(60) Division of application No. 10/612,818, filed on Jul. 1, 2003, now Pat. No. 6,933,123, and a continuation-in-part of application No. 09/828,645, filed on Apr. 5, 2001, now Pat. No. 6,743,593.

(60) Provisional application No. 60/394,172, filed on Jul. 2, 2002.

(51) Int. Cl.
    *G01N 33/53*    (2006.01)
(52) U.S. Cl. ........................... 435/7.1; 435/6; 435/7.91
(58) Field of Classification Search ............... 435/7.1, 435/6, 7.91
    See application file for complete search history.

(56) References Cited

U.S. PATENT DOCUMENTS

| | | | |
|---|---|---|---|
| 4,777,239 A | 10/1988 | Schoolnik et al. | |
| 5,629,146 A | 5/1997 | Dillner et al. | |
| 5,629,161 A | 5/1997 | Muller et al. | |
| 5,679,509 A | 10/1997 | Wheeler et al. | |
| 5,753,233 A | 5/1998 | Bleul et al. | |
| 5,932,412 A | 8/1999 | Dillner et al. | |
| 6,096,869 A | 8/2000 | Stanley et al. | |
| 6,183,746 B1 | 2/2001 | Urban et al. | |
| 6,783,763 B1 | 8/2004 | Choppin et al. | |
| 2005/0033025 A1* | 2/2005 | Choppin et al. | 530/350 |

FOREIGN PATENT DOCUMENTS

| | | |
|---|---|---|
| EP | 0 344 940 | 12/1989 |
| EP | 0 594 613 | 5/1994 |
| WO | WO87/01375 | 3/1987 |
| WO | WO91/18294 | 11/1991 |
| WO | WO99/10744 | 3/1999 |

OTHER PUBLICATIONS

Boryslewicz et al., *A recombinant vaccinia virus encoding human papillomavirus types 16 and 18 E6 and #7 proteins as immunotherapy for cervical cancer*, Lancet 1996; 347:1523-7.

Bryan et al., *Human Papillomavirus type 11 neutralization in the athymic mouse xenograft system: correlation with virus-like particle*, Journal of Med Virology 1997; 53:185-8.

Chee et al., *Immunologic diagnosis and monitoring of cervical cancers using in vitro translated HPV proteins*, Gynecology Oncology 1995; 57:226-231.

Clavel et al., *DNA-EIA to detect high and low risk HPV genotypes in cervical lesions with E6/E7 primer mediated multiplex PCR*, Journal of Clinical Pathology 1998; 51(1):38-43.

Cox et al., *Human papillomavirus testing by hybrid capture appears to be useful in triaging women with a cytologic diagnosis of atypical squamous cells of undetermined significance*. American Journal of Obstetrics and Gynecology 1995; 172:946-54.

Cuzick et al., *A systematic review of the role of human papillomavirus (HPV) testing within a crevical screening programme: summary and conclusions*, British Journal of cancer 2000; 85(5): 561-565.

Donnelly et al., *Protection against papillomavirus with a polynucleotide vaccine*, Journal of Infectious Diseases 1996; 713: 314-20.

Dreau et al., *Humanpapilloma virus in melanoma biopsy specimens and its relation to melanoma progression*; Annals of Surgery 2000; 231(5): 664-71.

Ferenczy et al., *Diagnostic performance of hybrid capture human papillomavirus deoxribonucleic acid assay combined with liquid-based cytologic study*, American Journal of Obstetrics and Gynecology 1996; 174(3): 651-6.

Frisch et al., *Human papillomavirus-associated carcinomas in Hawaii and the mainland U.S.*, Cancer 2000; 88: 1464-9.

Fu et al., *Human papillomavirus and papillomatosis lesion of female lower genital tract*, Infectious Disease Obstetrics and Gynecology 1994; 1:235-41.

(Continued)

*Primary Examiner*—Ali R. Salimi
(74) *Attorney, Agent, or Firm*—Pate Pierce & Baird

(57) ABSTRACT

An isolated protein sequence or peptide from the E2, E6 or E7 early coding region of human papillomavirus (HPV) that is soluble in an aqueous medium, and characterized by a relative paucity of tryptophan, methionine and cysteine residues, and a relative abundance of glycine and asparagine residues. Also disclosed are isolated protein sequences or peptides from the E2, E6 or E7 early coding regions of HPV 16 and 18 and methodologies for detecting or diagnosing cancer or cellular abnormalities. Detection or diagnosis of Cancer or cellular abnormalities may include detecting or diagnosing pre-cancerous or pre-malignant conditions, cervical dysplasia, cervical carcinoma, koilocytosis, hyperkeratosis, intraepithelial lesions, and other cancers. A methodology for detecting or diagnosing cancer or cellular abnormalities comprises the steps of (1) reacting a sample of body fluid or tissue with isolated protein sequences or peptides; (2) forming an antibody-peptide complex; and (3) detecting the antibody-peptide complex.

18 Claims, 2 Drawing Sheets

OTHER PUBLICATIONS

Fu et al., *Diagnosis between condyloma acuminatum and pseudocondyloma in lower female genital tract as determined by a PCR-based method*, Chinese Journal of Obstetrics and Gynecology 1994; 29(1): 168-88, [In Chinese; English abstract].

Gregoire et al., *Preferential association of human papillomavirus with high-grade histologic variants of penile-invasive squamous cell carcinoma*, Journal of the National Cancer Institute 1995; 87(22): 1705-9.

Hagensee et al., *Seroprevalence of human papillomavirus type 16 in pregnant women*, Obstetrics and Gynecology 1999; 94(5): 653-8.

Hamsikova et al., *Presence of antibodies to seven human papillomavirus type 16 derived peptides in cervical cancer patients and health controls*, Journal of Infectious Diseases 1994; 170: 1424-31.

Harlan et al., *Cervical cancer screening for cervical and breast cancer? Results from a New National Survey*, Archives of Internet Medicine 1988; 148: 1117-81.

Hayward et al., *Who gets screened for cervical and breast cancer? Results from a New National Survey*, Archives of Internal Medicine 1988; 148: 1117-81.

Hu Yx, *Introduction and prospect of application of biogenetic engineering*, Guangzhou Medical Journal 1990; 2:8-10 [In Chinese, English title].

Hutchinson et al., *Homogeneous sampling accounts for the increased diagnostic accuracy using the ThinPrep™Processor*, American Journal of Clinical Pathology 1994; 101: 215-9.

Jochmus et al., *Detection of antibodies to the E4 or E7 proteins of human papilloma-viruses (HPV) in human sera by western biot analysis: type specific reaction of anti-HPV 16 antibodies*, Molecular and Cellular Probes 1992; 6:319-25.

Kochel et al., *Antibodies to human papillomavirus type-16 in human sera as revealed by the use of prokaryotically expressed viral gene products*, Virology 1991; 182: 644-54.

Konya et al., *Antibodies to human papillomavirus type-16 in human sera as revealed by the use of prokaryotically expressed viral gene products*, Virology 1991; 182: 644-54.

Lorincz et al., *Human papillomavirus infection of the cervix: relative risk associations of 16 common anogenital types*, Obstetrics and Gynecology 1992; 79: 328-37.

Lowy et al., *Papillomaviruses: prophylactic vacine prospects*, Biochimica et biophysica Acta 1998; 1423: M1-8.

Mellin et al., *Human papilloma virus (HPV) DNA in tonsillar cancer: clinical correlates, risk of relapse, and survival*, International Journal of Cancer (Pred. Oncol.) 2000; 89: 300-4.

Meschede et al., *Antibodies against early proteins of human papillomaviruses as diagnostic markers for invasive cervical cancer*, Journal of Clinical Microbiology 1998; 36(2): 475-80.

Muller et al., *Antibodies to the E4, E6 and E7 proteins of human papillomavirus (HPV) type 16 in patients with HPV-associated disease and in the normal population*, Journal of Investigative Dermatology 1995; 104: 138-41.

Nobbenhuis et al., *Relation of human papillomavirus status to cervical lesions and consequences for cervical-cancer screening: a prospective study*, Lancet 1999; 354: 20-5.

Petter et al., *Specific serum IgG, Igm and IgA antibodies to human papillomavirus types 6, 11, 16, 18 and 31 virus-like particles in human immunodeficiency virus-seropositive women*, Journal of General Virology 2000; 81: 701-8.

Pirog et al., *Prevalence of human papillomavirus DNA in different histological subtypes of cervical adenocarcinoma*, American Journal of Pathology 2000; 157(4): 1055-62.

Rice et al., *High risk genital papillomavirus infections are spread vertically*, Review of Medical Virology 1999; 9: 15-21.

Schiffman Mh, *Recent progress in defining the epidemiology of human papillomavirus infection and cervical neoplasia*, Journal of the National Cancer Institute 1992; 84(6): 394-8.

Silins et al., *Serological evidence for protection by human papillomavirus (HPV) type 6 infection against HPV type 16 cervical carcinogenesis*, Journal of General Virology 1999; 80: 2931-6.

Slawson et al., *Follow up papanicolau smear for cervical atypia: we are missing significant disease? A HARNET study*, Journal of Family practice 1993; 36(3): 289-93.

Soini et al., *Presence of human papillomavirus DNA and abnormal p53 protein accumulation in lung carcinoma*, Thorax 1996; 51: 887-93.

Suga seet al., *Serum antibodies to human papillomavirus 16 proteins in women from Brazil with invasive cervical carcinoma*, Cancer Epidemiology, Biomarkers & Prevention 1999; 8: 935-40.

Sun et al., *Serum antibodies to human papillomavirus 16 proteins in women from Brazil with invasive cervical carcinoma*, Cancer Epidemiology, Biomarkers & Prevention 1999; 8: 935-40.

Verdon Me, *Issues in the management of human papillomavirus genital disease*, American Family Physician 1997; 55: 1813-16.

Walboomers et al., *Human papillomavirus is a necessary cause of invasive cervical cancer worldwide*, Journal of Pathology 1999; 189: 12-19.

Wright et al., HPV CNA *Testing of self-collected vaginal samples compared with cytologic screening to detect cervical cancer*, Journal of the American Medical Association 2000; 283: 81-6.

Zumbach et al., *Antibodies against oncoproteins E6 and E7 of human papillomavirus types 16 and 18 in patients with head-and-neck squamous-cell carcinoma*, International Journal of Cancer 2000; 85: 815-8.

* cited by examiner

Table 1. Pap Smear Cytology, Digene HPV DNA Hybrid Capture Assay Results, and Diagnosis or Status Regarding Dysplasia from Subjects Tested for Cervical Disease Via Enzyme-Linked Immunosorbent Assay (ELISA) Using Peptides Comprising Invention.

| Subject Number | Pap Smear Interpretation[1] | Digene HPV Hybrid Capture[2] | Diagnosis or Status[3] |
|---|---|---|---|
| 1 | Not done | Not done | Virgin, 14 years old |
| 2 | Not done | Not done | Virgin, 15 years old |
| 3 | No cell abnormalities found | Negative | No history of dysplasia |
| 4 | No cell abnormalities found | Negative | No history of dysplasia |
| 5 | No cell abnormalities found | Negative | No history of dysplasia |
| 6 | No cell abnormalities found | Negative | No history of dysplasia |
| 7 | Cell abnormalities present | Negative | CIN I |
| 8 | No cell abnormalities found | Positive | CIN II |
| 9 | Cell abnormalities present | Positive | CIN II |
| 10 | Cell abnormalities present | Positive | CIN III |
| 11 | Cell abnormalities present | Positive | CIN III |
| 12 | Cell abnormalities present | Positive | CIN III |
| 13 | Cell abnormalities present | Positive | Squamous cell carcinoma |
| 14 | Cell abnormalities present | Positive | Squamous cell carcinoma |
| 15 | No cell abnormalities found | Positive | Adenocarcinoma |
| 16 | Cell abnormalities present | Positive | Adenocarcinoma |

[1] ThinPrep slide interpreted by a Board Certified Cytopathologist

[2] DNA test for ascertaining presence/infection by "oncogenic" HPVs

[3] Where applicable, includes diagnosis or status after taking into account results from colposcopy and biopsy; CIN = Cervical Intraepithelial Neoplasia; CIN I = mild abnormalities that rarely develop into cervical cancer; CIN II = lesions appearing more aggressive under the microscope, involving about one-half of the thickness of the surface lining of the cervix; CIN III = the most aggressive form of dysplasia in which the entire surface lining is abnormal, high probability of progressing to invasive cancer if not removed and includes carcinoma in situ.

Fig. 1

Table 2. Absorbance Values for Enzyme-Linked Immunosorbent Assays, or ELISAs, Using Peptides Comprising Invention. A reaction, oxidation of the bound enzyme-labeled antibody-antigen complex, produces a color for which intensity is proportional to the amount of antibody in the serum sample. Detection and quantification were done with absorbance at 450 nm, with values rounded to the nearest hundredths of absorbance units.

| Subject Number | SEQUENCE ID NUMBER (SEQ ID NO:) | | | | | | | |
|---|---|---|---|---|---|---|---|---|
| | 1 | 2 | 3 | 4 | 5 | 6 | 7 | 8 |
| Blank Control | 0.04 | 0.05 | 0.04 | 0.04 | 0.03 | 0.04 | 0.04 | 0.05 |
| 1 | 0.14 | 0.20 | 0.19 | 0.17 | 0.17 | 0.18 | 0.24 | 0.20 |
| 2 | 0.17 | 0.14 | 0.21 | 0.20 | 0.17 | 0.15 | 0.18 | 0.16 |
| 3 | 0.20 | 0.16 | 0.15 | 0.11 | 0.20 | 0.21 | 0.16 | 0.22 |
| 4 | 0.23 | 0.18 | 0.18 | 0.24 | 0.15 | 0.23 | 0.25 | 0.13 |
| 5 | 0.20 | 0.17 | 0.23 | 0.14 | 0.24 | 0.18 | 0.15 | 0.20 |
| 6 | 0.44 | 0.32 | 0.49 | 0.17 | 0.24 | 0.21 | 0.19 | 0.22 |
| 7 | 0.21 | 0.24 | 0.18 | 0.18 | 0.18 | 0.23 | 0.14 | 0.19 |
| 8 | 0.40 | 0.34 | 0.51 | 0.49 | 0.57 | 0.40 | 0.46 | 0.53 |
| 9 | 0.44 | 0.25 | 0.29 | 0.43 | 0.27 | 0.53 | 0.44 | 0.24 |
| 10 | 0.31 | 0.36 | 0.32 | 0.56 | 0.44 | 0.41 | 0.53 | 0.35 |
| 11 | 0.32 | 0.33 | 0.29 | 0.41 | 0.46 | 0.48 | 0.41 | 0.37 |
| 12 | 0.14 | 0.50 | 0.26 | 0.58 | 0.38 | 0.53 | 0.42 | 0.41 |
| 13 | 0.19 | 0.24 | 0.37 | 0.49 | 0.50 | 0.63 | 0.44 | 0.47 |
| 14 | 0.31 | 0.39 | 0.43 | 0.60 | 0.51 | 0.55 | 0.46 | 0.50 |
| 15 | 0.36 | 0.40 | 0.45 | 0.44 | 0.61 | 0.44 | 0.55 | 0.59 |
| 16 | 0.35 | 0.21 | 0.28 | 0.40 | 0.47 | 0.39 | 0.44 | 0.48 |

Kruskal--Wallis one-way analysis of variance on samples of unequal size:

Absorbance Values for Subjects 1-6 versus Absorbance Values for Subjects 7-16, $p < 0.001$ (Extremely Significant)

Conclusion: Subjects with mild to severe cervical dysplasia and cancer have significantly greater antibody titers with respect to peptides of invention than do non-diseased or healthy subjects.

Fig. 2

PEPTIDES FROM THE E7 PROTEIN OF HUMAN PAPILLOMA VIRUSES 16 AND 18 FOR DETECTING AND/OR DIAGNOSING CERVICAL AND OTHER HUMAN PAPILLOMA VIRUS ASSOCIATED CANCERS

RELATED APPLICATIONS

This application claims the benefit of Divisional U.S. patent application Ser. No. 10/612,818, filed Jul. 1, 2003, now U.S. Pat. No. 6,933,123 and entitled "PEPTIDES FROM THE E2, E6, AND E7PROTEINS OF HUMAN PAPILLOMAVIRUSES 16 AND 18 FOR DETECTING AND/OR DIAGNOSING CERVICAL AND OTHER HUMAN PAPILLOMAVIRUS ASSOCIATED CANCERS" which claims the benefit of U.S. Provisional Application Ser. No. 60/394,172, filed Jul. 2, 2002, and entitled "NOVEL PEPTIDES FROM THE E2, E6 AND E7 PROTEINS OF HUMAN PAPILLOMAVIRUSES 16 AND 18 FOR DIAGNOSING OR DETECTING CERVICAL AND OTHER HUMAN PAPILLOMAVIRUS ASSOCIATED CANCERS," and CIP of co-pending U.S. patent application Ser. No. 09/828,645, filed Apr. 5, 2001, now U.S. Pat. No. 6,743,593 and entitled "IMMUNOLOGICAL METHODOLOGY FOR DISCERNING HUMAN PAPILLOMAVIRUS," which are incorporated herein by reference.

BACKGROUND

1. Field of the Invention

The present invention relates generally to the field of peptides reactive with antibodies formed against human papillomavirus (HPV). Some have termed this type of peptide as antigenic or immunoreactive. More particularly, the invention relates to peptides isolated, purified or derived from the early coding region of the E2, E6, and E7 oncoproteins of HPV and method for use for the detection and/or diagnosis of HPV associated epithelial cell abnormalities, precancerous conditions and cancers via an immunoassay.

2. The Background Art

The human papillomaviruses (HPV), named because certain types induce warts or papillomas, cause virtually all cervical cancers (Nobbenhuis et al., "Relation of human papillomavirus status to cervical lesions and consequences for cervical-cancer screening: a prospective study," The Lancet, 354:20-25, 1999; Cuzick et al., "A systematic review of the role of human papilloma virus (HPV) testing within a cervical screening programme: summary and conclusions," British Journal of Cancer, 83:561-565,2000). These encompass not only squamous cell carcinomas (Nobbenhuis et al., 1999) but also adenocarcinomas (Pirog et al., "Prevalence of human papillomavirus DNA in different histological subtypes of cervical adenocarcinoma," American Journal of Pathology, 157:1055-1062, 2000). These viruses are also strongly associated with vulvar and vaginal carcinomas (Frisch et al., "Human papillomavirus-associated carcinomas in Hawaii and the mainland US," Cancer 88:1464-1469, 2000; Sugase et al., "Distinct manifestations of human papillomaviruses in the vagina," International Journal of Cancer, 72:412-415, 1997), as well as cancers of the anus (Frisch et al., 2000) and penis (Gregoire et al., "Preferential association of human papillomavirus with high-grade histologic variants of penile-invasive squamous cell carcinoma," Journal of the National Cancer Institute, 87:1705-1709, 1995).

Moreover, HPV may be responsible for certain carcinomas in the head and neck region (Mellin et al., "Human papillomavirus (HPV) DNA in tonsillar cancer: clinical correlates, risk of relapse, and survival," International Journal of Cancer, 89:300-304, 2000; Zumbach et al., "Antibodies against oncoproteins E6 and E7 of human papillomavirus types 16 and 18 in patients with head-and-neck squamous-cell carcinoma," International Journal of Cancer, 85:815-818, 2000), seem associated with the more deadly melanomas (Dreau et al., "Human papillomavirus in melanoma biopsy specimens and its relations to melanoma progression," Annals of Surgery, 231:664-671, 2000), and could play a role in lung carcinomas (Soini et al., "Presence of human papillomavirus DNA and abnormal p53 protein accumulation in lung carcinoma," Thorax 51:887-893, 1996) and perhaps other cancers.

Cervical cancer is the second most common cancer among women worldwide. Each year about 450,000 women worldwide are diagnosed with cervical cancer, and nearly 300,000 women die of this disease. Since the advent of organized cervical cancer screening by cytology fifty (50) years ago, the mortality rate of cervical cancer has dramatically decreased in developed countries. In fact, cervical cancer may be considered preventable. In this regard, an important key to prevention is the timely identification and management of precancerous lesions and otherwise early cancers through accessible and affordable screening programs and methodologies.

At present, about twelve percent (12%) of female cancers worldwide are due to HPV infections of the cervix. There is consensus among the medical community that oncogenic HPV detection would be an effective way to identify cancer victims or those at high risk for the disease. Notably, HPV detection would facilitate earlier detection of cancer or cellular abnormalities suggesting cancer at a point in time when the cancer or cellular abnormalities exists at a more readily curable stage.

A primary methodology for public health screening for cervical cancer has been the Papanicolaou (Pap) smear. For a variety of reasons, the Papanicolaou smear is less than an ideal screening test. Drawbacks may include difficulty of obtaining samples, high rate of false negatives (up to twenty percent (20%)), and requirements for specialized labs staffed by highly trained personnel. Nucleic acid screening methods have been developed by those skilled in the art, but are not ideal primarily due to their high cost and like requirement for highly trained personnel. Another assay developed by those skilled in the art involves the so-called "DNA Hybrid Capture." This method, however, tends to suffer from high cost and sampling difficulties, thus making it somewhat disadvantageous as an ideal screening test.

Recently, those skilled in the art have developed methodologies for examining the utility of HPV for diagnostic purposes. More particularly, IgA, IgG and IgM antibodies raised against HPV have been used in the detection of infection with HPV and for diagnosing carcinoma or pre-stages thereof. Using these prior art techniques, immunoreactive peptides isolated from HPV have been defined to have an epitope which is reactive with human sera. The prior art does not, however, disclose the peptides of the present invention, nor teach that multiple combinations of antibody-epitope complexes could be contemplated to produce diagnostic assays with improved sensitivity and/or specificity.

Such prior art methods for cancer screening, are limited by their cost, sampling procedures, accuracy, equipment and personnel requirements. Therefore, and as readily appreciated by those skilled in the art, low cost, simple, sensitive and specific assays that can be performed on readily obtainable bodily samples would be a significant advancement in the art. Such assays are disclosed and claimed herein.

BRIEF SUMMARY AND OBJECTS OF THE INVENTION

A primary object of the present invention is to provide novel antibody reactive protein sequences or peptides isolated, purified or derived from the HPV 16 and 18 E2 protein and the HPV 16 and 18 E6 and E7 oncoproteins.

It is a further object to provide these peptides in a chemically pure form.

A further object to provide a simple, rapid, less expensive and more sensitive test for detecting or diagnosing not only HPV infections, but also most, if not all, HPV associated neoplasms.

It is a still further object is to provide antigens for use in HPV inoculums that will induce antibody production and killer T cell activity.

It is also an object of the present invention to provide novel antibody reactive protein sequences or peptides isolated, purified or derived from HPV genotypes 16, 18, 31, 33, 35, 45, 51, 52, 56 and 58.

In addition, it is an object of the present invention to provide novel antibody reactive protein sequences or peptides isolated, purified or derived from HPV further comprising one or more additional glycine residues added at a carboxyl terminal residue end of the protein sequence or peptide.

It is a still further object of the present invention to provide novel antibody reactive protein sequences or peptides isolated, purified or derived from HPV further comprising one or more additional asparagine residues added at a carboxyl terminal residue end of the protein sequence or peptide.

It is another object of the present invention to provide novel antibody reactive protein sequences or peptides isolated, purified or derived from HPV further comprising a combination of glycine and asparagine residues added at a carboxyl terminal residue end of the protein sequence or peptide.

Further, it is an object of the present invention to provide a method for detecting or diagnosing cancer or cellular abnormalities comprising the steps of reacting a sample of body fluid or tissue likely to contain antibodies with one or more protein sequences or peptides isolated from the E2, E6 and E7 early coding regions of HPV; forming an antibody-peptide complex comprising an antibody and a protein sequence or peptide isolated from the E2, E6 and E7 early coding region of HPV; and detecting said antibody-peptide complex.

It is a still further object of the present invention to provide novel antibody reactive protein sequences or peptides isolated, purified or derived from HPV further comprising substitution of one or more cysteine residues with one or more carboxymethylcellulose residues.

Additionally, it is an object of the present invention to provide a method for detecting or diagnosing cancer or cellular abnormalities through detection or diagnosis of an HPV Epitope.

It is also an object of the present invention to provide a method for detecting or diagnosing cancer or cellular abnormalities through detection or diagnosis of HPV associated cell abnormalities.

It is a further object of the present invention to provide a method for detecting or diagnosing cancer or cellular abnormalities through detection or diagnosis of HPV associated precancerous or premalignant conditions.

It is a still further object of the present invention to provide a method for detecting or diagnosing cancer or cellular abnormalities through detection or diagnosis of cervical dysplasia.

Additionally, it is an object of the present invention to provide a method for detecting or diagnosing cancer or cellular abnormalities through detection or diagnosis of cervical carcinoma.

It is also an object of the present invention to provide a method for detecting or diagnosing cancer or cellular abnormalities through detection or diagnosis of adenocarcinoma of the uterine cervix.

Further, it is an object of the present invention to provide a method for detecting or diagnosing cancer or cellular abnormalities through detection or diagnosis of HPV associated precancerous or premalignant conditions.

It is a still further object of the present invention to provide a method for detecting or diagnosing cancer or cellular abnormalities through detection or diagnosis of cervical dysplasia.

Consistent with the foregoing objects, and in accordance with the invention as embodied and broadly described herein, one presently preferred embodiment of the present invention comprises novel peptides, the sequences of which were isolated from careful analysis of the early coding regions of the E2, E6 and E7 oncoproteins of HPV 16 and 18. The peptides may lend themselves to a highly sensitive and specific diagnostic immunoassay. Antibodies to the E2, E6 and E7 oncoproteins may be found in those individuals infected with HPV associated neoplasms.

The peptides of the present invention, ranging in size, prior to any modifications, from about 17 amino acid residues to about 23 amino acid residues may be readily synthesized by chemical means and may be obtained at purities exceeding 95%. Although the peptides may be obtained by other means, in their pure form there is typically a much reduced likelihood for undesirable cross reactivity with random antibodies. Hence, the pure peptides of the present invention may lend themselves to diagnostic immunoassays of high specificity. One presently preferred embodiment of a diagnostic immunoassay method of the present invention may include the steps of: (1) taking a sample of body fluid or tissue likely to contain antibodies; (2) if antibodies are present, reacting the sample with one or more of the peptides of the present invention; and (3) assaying the reacted sample for the presence of an antibody-peptide reaction.

Immunoassays employing the peptides isolated, purified or derived from the E6 and the E7 oncoproteins of HPV 16 and 18 may serve as reliable indicators that HPV associated malignancy or premalignant cell transformation has taken place. Likewise, immunoassays employing certain peptides isolated, purified or derived from the E2 region of HPV 16 and 18 may also be reliable indicators of HPV associated infection, malignacy or prelmalignant cell transformation.

One of the most useful advancements or aspects of the present invention is in diagnosing cervical carcinoma, both squamous cell and adenocarcinoma, as well as any epithelial cell abnormality associated with oncogenic HPV infection including, but not limited to, koilocytosis; hyperkeratosis; precancerous conditions encompasssing intraepithelial neoplasias or intraepithelial lesion; high-grade dysplasias; and invasive or malignant cancers. Besides its utility in cervical cancer diagnoses, finding antibodies to peptides isolated, purified or derived from the HPV E2, E6 and E7 oncoproteins of HPV 16 and 18 may be valuable for detecting head and neck cancers, small cell lung cancers, penile and anal carcinomas, melanoma and other precancerous or cancerous states caused by or otherwise associated with HPV.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 1 represents a table showing the results of Pap smear cytology and diagnostic immunoassay applying HPV DNA Hybrid Capture on subjects with and without HPV associated dysplasia or otherwise premalignant conditions as well as cancer;

FIG. 2 represents a table further showing the results of a diagnostic immunoassay applying the peptides of the present invention on subjects with and without HPV associated dysplasia or otherwise premalignant conditions as well as cancer.

DESCRIPTIONS OF THE PREFERRED EMBODIMENTS

It will be readily understood that the isolated protein sequences and methodologies of the present invention, as generally described and illustrated in the Figures herein, could be arranged and designed in a wide variety of different configurations. Those of ordinary skill in the art will, of course, appreciate that various modifications to the details herein may be made without departing from the essential characteristics of the invention, as described. Thus, the following more detailed description of the embodiments of the isolated protein sequences and methodologies of the present invention, as represented in FIGS. 1 and 2, is not intended to limit the scope of the invention, as claimed, but it is merely representative of the presently preferred embodiments of the invention.

HPV exists as different genetic types or genotypes, designated by numbers, concerning which only a subset is oncogenic or cancer causing. Over 100 HPV genotypes have been identified. These HPV genotypes are sometimes referred to as HPV strains or types and are often designated or referred to by number only or by "HPV #", where "#" is the number of the oncogenic or cancer causing genotype. Cancers overwhelmingly stem from HPV 16 and 18, but may also be associated with HPV 31, 33, 35, 45, 51, 52, 56 and 58. The virus infects cervical and other cells that generally support virus propagation, where it may cause abnormal cellular changes that can lead to life threatening malignancies.

HPV infection requires cells that are able to replicate their DNA, specifically those cells in the basal epidermal layer. HPV entry into the basal epidermal layer occurs through microlesions that expose basal proliferating cells to the surface. The virus attaches to a cell surface receptor and gains entry into the cell cytosol. The infecting HPV particle contains a closed-circular double-stranded DNA genome of 7000 to 8000 base pairs composed of eight early transcribed open reading frames, E1 to E8, sometimes referred to as early coding regions and which are unequally represented among HPV genotypes, two late open reading frames and a noncoding long control region.

Much has been discovered about how HPV DNA integrates into host chromosomes and how the E1 and E2 oncoproteins are involved with this process. Relevance to immunological diagnostics is that antibodies against E1 and E2 gene products may be evidence that HPV infection has occurred.

The manner by which HPV infection leads to cancer includes cellular interactions with the E6 and E7 gene products. Stated another way, the E6 and E7 genes encode amino acids which are translated into protein sequences or peptides, which then interact with cell structures or proteins and may lead to cancer. Gene products which may lead to tumor or cancer are often referred to as being oncogenic proteins or oncoproteins.

In host cells, E6 and E7 gene products form complexes with the cellular p53 and retinoblastoma tumor suppressing proteins regulating cell division. By functionally neutralizing or inactivating these proteins, cells enter into the S phase of the cell cycle. The E7 oncoprotein further destabilizes cell control through its interaction with the cyclin-dependent kinase inhibitor protein, p21. These interactions set the stage for controlling host cell proliferation and differentiation (i.e., transformation), a first step in the conversion of normal cells to preneoplastic (i.e., pre-cancerous) cells and ultimately to the full expression of malignancy or cancer.

The E6 and E7 oncoproteins are constitutively expressed in tumor cells, and silencing these genes yields reversion of the malignant phenotype. Thus, the E6 and E7 gene products seem tumor-specific antigens, and possible targets or probes for antibodies in immunological cancer tests as well as antigens in vaccines for controlling HPV-induced tumors.

Indeed, the E6 and E7 oncoproteins appear natural targets for antibody production due to their consistent expression in cervical cancer cells. The response against the E7 oncoprotein in earlier studies had only been moderately disease specific, but E7 IgG and IgA have now been verified as strongly disease associated. Antibodies against the E6 and E7 oncoproteins are at high levels in sera from cervical cancer patients compared against non-cancer controls. Moreover, such antibodies seem detectable by immunological means even when present in lesser amounts. Sensitivity for identifying HPV infections and possible cancers increases with a combination of serological tests of multiple virus proteins. Hence, using both oncoproteins yields positive immunological results with samples from cervical cancer patients.

In addition to the methodologies of the present invention, it may also be advantageous to employ an detection or diagnostic methodology utilizing a combination of gene products, protein sequences or peptides from two or more of the HPV E2, E6 and E7 early coding regions. A combination of isolated protein sequences or peptides from HPV E2 with HPV E6 or E7 may allow for more sensitive and/or more specific methodologies for detecting or diagnosing HPV virus integration (i.e.,infection) into a host cell as well as detecting or diagnosing HPV associated cellular abnormalities. Alternatively, a combination of isolated protein sequences or peptides from HPV E6 with HPV E7 may allow for more sensitive and/or more specific methodologies for detecting or diagnosing certain cellular abnormalities.

Antibodies against E2 may also be associated with premalignant states and cancer (Stevenson et al., "Inverse relationship between the expression of the human papillomavirus type 16 transcription factor E2 and virus DNA copy number during the progression of cervical intraepithelial neoplasias", Journal of General Virology, 81:1825-1832, 2001; Tonon et al., "Physical status of the E2 human papilloma virus 16 viral gene in cervical preneoplastic and neoplastic lesions", Journal of Clinical Virology, 21:129-134, 2001; Lindel et al., "Human papillomavirus positive squamous cell carcinoma of the oropharynx: a radiosensitive subgroup of head and neck carcinoma", Cancer, 92:805-813, 2001; Rosales et al., Antibodies against human papillomavirus (HPV) type 16 and 18 E2, E6 and E7 proteins in sera: correlation with presence of papillomavirus DNA", Journal of Medical Virology, 65:736-744, 2001; Sheets et al., "Immunotherapy of human cervical high-grade cervical intraepithelial neoplasia with microparticle-delivered human papillomavirus 16 E7 plasmid DNA", American Journal of Obstetrics and Gynecology, 188:916-926, 2003), but specific details as to how the HPV E2 protein contributes to oncogenesis still remain obscure (Dong et al., "Human papillomavirus type 11 E2 proteins repress the homologous E6 promoter by interfering with the binding of host transcription factors to adjacent elements", Journal of Virology, 68:1115-1127, 1994).

The protein sequences or peptides of the present invention may be isolated, purified or derived from the early coding regions of the E2, E6, and E7 oncoproteins of HPV 16 and 18. The isolation of the peptides of the present invention may be based on their ability to react with antibodies formed in a host infected with oncogenic HPV. Among the specific factors used in the selection process is solubility in aqueous solution or hydrophilic nature. It was assumed that hydrophilic regions of the oncogene product protein were more likely oriented toward the surface of the complete protein under natural or native conditions, and that such consequently include antigenic regions against which antibody reactivity would most likely occur.

Antigenic describes a substance that the body regards as foreign or potentially dangerous and against which the body produces an antibody. Typically, an antigen is composed of a protein or peptide. An antibody is a specialized protein produced in the lymphoid tissue in response to the presence of a particular antigen. The antibody will attack the antigen and render it harmless. The antibody attack typically leads to the formation of an antigen-antibody complex and is often interchangeably used with the terms, antibody-peptide complex or peptide-antibody complex and antibody-epitope complex.

Another factor is that an overall relative paucity of cysteine residues in the amino acid sequence be maintained. More than one cysteine at the amino terminal residue was considered unacceptable. Attempts were also made to limit cysteine elsewhere along the peptide, since multiple cysteines could portend circumstances precluding usefulness in an immunoassay. Peptides with cysteine are more susceptible to oxidation at a neutral pH, and the propensity for cysteines to undergo sulphydryl formation could lead to a dimerization that impedes antibody binding.

In addition, there was looked for an overall paucity of tryptophan, due to the elevated oxidative potential of this amino acid. By paucity, it is meant that there are as few occurrences as possible and by abundance, it is meant that there is no limit on the number of occurrences in the sequence. A still more preferred embodiment of the peptide compositions includes up to eight additional amino acid residues attached to the carboxyl terminal residue where those residues are any combination of glycine and asparagine. Additional glycine and asparagine amino acid residues may help orient the peptide in aqueous medium such that binding to antibody may be enhanced.

Eight specific protein sequences or peptides ranging from 17 to 23 amino acid residues in length, may be isolated, purified or derived from the E2, E6 and E7 oncoproteins of HPV 16 and HPV 18, as defined hereinbelow. Sequence Identification Number (SEQ. ID. No.) 1 was derived from the E2 Region of HPV 18. Decoded and using the standard three letter acronym, Sequence Number 1, comprised of the 22 residues making up amino acids 219 through 240 of the HPV 18 E2 oncoprotein, is as follows, with the sequence beginning at the amino terminal residue and ending at the carboxyl terminal residue:

```
                                                            (SEQ. ID. NO.1)
         Lys Gln Leu Gln His Thr Pro Ser Pro Tyr Ser Ser Thr Val Ser Val
         1               5                   10                  15

Gly Thr Ala Lys Thr Tyr
                     20
```

Sequences numbers 2 and 3 are derived from the E2 early coding region of HPV 16. Decoded using the standard three letter abbreviations, Sequence Number 2, comprised of the 17 residues making up amino acids 112 through 131 of the HPV 16 E2 oncoprotein, and Sequence Number 3, comprised of the 23 residues making up amino acids 187 through 209 of the HPV 16 E2 oncoprotein, are as follows, with the sequence beginning at the amino terminal residue end:

```
                                                            (SEQ. ID. NO. 2)
         Lys His Gly Tyr Thr Val Gln Phe Asp Gly Ile Cys Asn Thr Met His
         1               5                   10                  15

Tyr
```

```
                                                            (SEQ. ID. NO. 3)
         His Ala Gly Gly Gln Val Ile Leu Cys Pro Thr Ser Val Phe Ser Ser Asn
         1               5                   10                  15

Glu Val Ser Ser Pro Glu
                     20
```

Sequence number 4 is derived from the E6 early coding region of HPV 16. Decoded using the standard three letter abbreviations Sequence Number 4, comprised of the 22 residues making up amino acids 62 through 83 of the HPV 16 E6 oncoprotein, is as follows, with the sequence beginning at the amino terminal residue end:

```
                                                        (SEQ. ID. NO. 4)
Arg Asp Gly Asn Pro Tyr Ala Val Cys Asp Lys Cys Leu Lys Phe Tyr
1               5                   10                  15

Ser Lys Ile Ser Glu Tyr
            20
```

Sequence number 5 is derived from the E6 early coding region of HPV 18. Decoded using the standard three letter abbreviations, Sequence Number 5, comprised of the 22 residues making up amino acids 67 through 88 of the HPV 18 E6 oncoprotein, is as follows, with the sequence beginning at the amino terminal residue end:

```
                                                        (SEQ. ID. NO. 5)
Lys Cys Ile Asp Phe Gly Ser Arg Ile Arg Glu Leu Arg His Tyr Ser
1               5                   10                  15

Asp Ser Val Tyr Gly Asp
            20
```

Sequences numbers 6 and 7 are derived from the E7 early coding region of HPV 16. Decoded using the standard three letter abbreviations, Sequence Number 6, comprised of the 21 residues making up amino acids 26 through 46 of the HPV 16 E7 oncoprotein, and Sequence Number 7, comprised of the 21 residues making up amino acids 67 through 88 of the HPV 16 E7 oncoprotein, are as follows, with the sequences beginning at the amino terminal residue end:

```
                                                        (SEQ. ID. NO. 6)
Glu Gln Leu Asn Asp Ser Ser Glu Glu Glu Asp Glu Ile Asp Gly Pro
1               5                   10                  15

Ala Gly Gln Ala Glu
            20
```

```
                                                        (SEQ. ID. NO. 7)
Glu Thr Thr Asp Leu Tyr Cys Tyr Glu Gln Leu Asn Asp Ser Ser Ser
1               5                   10                  15

Glu Asp Glu Ile Asp
            20
```

Sequence number 8 is derived from the E7 early coding region of HPV 18. Decoded using the standard three letter abbreviations, Sequence Number 8, comprised of the 22 residues making up amino acids 14 through 35 of the HPV 18 E7 oncoprotein, is as follows, with the sequence beginning at the amino terminal residue end:

```
                                                        (SEQ. ID. NO. 8)
His Leu Gln Pro Gln Asn Glu Ile Pro Val Asp Leu Leu Cys His Glu
1               5                   10                  15

Gln Leu Ser Asp Ser Glu
            20
```

The use of the peptides in a diagnostic method is based on the fact that antibodies to the native epitopes of the E2, E6, and E7 oncoproteins of HPV 16 and 18 are found in those suffering from a variety of HPV associated cell abnormalities that exist in neoplasms, from precancerous states to malignancy. More particularly, such HPV associated cellular abnormalities or dysplasias may include, but are not necessarily limited to, koilocytosis; hyperkeratosis; precancerous conditions encompassing intraepithelial neoplasias or intraepithelial lesions; high-grade dysplasias; and invasive or malignant cancers. Dysplasia generally refers to the presence or development of abnormal, premalignant or precancerous cells. The malignant neoplasms associated with HPV are discussed above.

The diagnostic method comprises taking a sample of body fluid or tissue likely to contain antibodies. This sample is preferably easy to obtain and may be serum or plasma derived from a venous blood sample or even from a finger prick. However, cervical secretions, cervical tissue, tissue from other body parts, or other bodily fluids are known to contain antibodies and may be used as a source of the sample. Once the peptide antigen and sample antibody are permitted to react in a suitable medium, an assay is then performed to determine to presence of an antibody-peptide reaction.

The following example will illustrate the practice of the present invention in further detail. It will be readily understood by those skilled in the art that the following methods, formulations, and compositions of novel peptides from the early coding regions of E2, E6 and E7 of HPV 16 and 18 of the present invention, as generally described and illustrated in the Examples herein, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Example I, is not intended to limit the scope of the invention, as claimed, but is merely representative of presently preferred embodiments of the invention.

EXAMPLE I

1. Synthesis of the Amino Acid Sequences or Peptides

While the peptides of the invention may be obtained by a variety of prior art methods, including, but not limited to recombinant technology and other biotechnology sources, chemical synthesis is the preferred method as it facilitates the accumulation of a sizable quantity of peptide in a substantially pure form, 95 to 99% by weight in the present case. The synthesis of peptides may be accomplished on a 0.25 scale using (9-fluorenyl) methoxycarbonyl (FMOC)-protected L-amino acids, with super acid-labile 2-chlorotrityl resin (Novabiochem, Nottingham, UK) as a solid support. A Resin may be preloaded into a reaction vessel, washed with dimethyl formamide and then drained completely. To this resin may be added 10 ml of 20% piperidine in dimethyl formamide. The mixture may then be shaken for 5 minutes and drained. Another 10 ml of 20% piperidine in dimethyl formamide may be added, and the mixture shaken for 30 minutes. After draining, the resin may be washed with dimethyl formamide four times, and then once with dichloromethane. The resin beads may be considered appropriately prepared if these turned blue using the standard ninhydrin test.

For each amino acid a coupling solution may be prepared, as follows: 1 mmol Fmoc Amino Acid of choice; 2.1 mL 0.45 M 2-(1H-benzotriazole-1-yl)-1,1,3,3-tetramethyluronium-hexafluoro-phosphate/hydrobenzotriazole [1 mmol]; 348 µL of N,N-diisopropylethylamine [2 mmol]. The mixture may be shaken for a minimum of 30 minutes. The reaction vessel may be drained and the resin washed four times with dimethylformamide, and a final time with dichloromethane. A standard ninhydrin test may be performed to ascertain coupling of the amino acid. For each amino acid, coupling solution may be added to the resin in the appropriate order, with the coupling reaction repeated until all amino acids may be in place along the peptide.

The completed peptide may be cleaved from the resin by reaction for two hours with a solution of 5% H2O, 5% phenol, 3% thioanisole, 3% ethanedithiol, 3% triisopropylsilane, 81% trifluoroacetic acid. After cleavage, the resin mixture may be filtered into cold methyl-tbutyl-ether. The precipitated peptide may then be washed twice with cold methyl-tbutyl-ether and dried under gaseous nitrogen. The molecular weight of the peptide may be checked by Matrix-Assisted laser Desorption Time-of Flight Mass Spectrometry, and the purity by High Performance Liquid Chromatography using a C18300A 5 µ column. The synthesized peptide sequences may be about at a 95 to 99% level of purity, but it is emphasized that lesser levels may be considered possibly appropriate for assay purposes.

2. Storage of the Amino Acid Sequences

The manufactured amino acid sequences may be suspended in PBS at about pH 7.0 to a concentration of about 1 mg/mL and may be stored in sealed vials at about −20° C.

3. Maleic Anhydride Binding of the Amino Acid Sequences to Titer Plates

REACTI-BIND™ Maleic Anhydride Activated Polystyrene Plates (Pierce, Rockford, Ill.) may be employed. Each amino acid sequence may be diluted to 12.5 µg/mL with coating buffer (100 mM sodium bicarbonate buffer, pH 9.4). To each titer well, 100 µL (1.25 µg) of the diluted sequence solution may be added. The plate may then be incubated for one hour at room temperature with shaking. The plate may be emptied and residual liquid tapped onto a clean paper towel. Each well may be washed with 100 µL wash buffer (0.1% bovine serum albumin and 0.05% Tween-20 in phosphate buffered saline, pH 7.0). This may be repeated for a total of three times. Each time, the plate may be emptied and residual liquid tapped onto a clean paper towel. To each well, 200 µL of blocking solution (3% bovine serum albumin and 0.05% Tween-20 in phosphate buffered saline, pH 7.0) may be added.

Blocking solution may be left in each well for one minute. The titer plate may then be emptied by inversion. Filling with blocking solution and emptying may be done three times. Finished titer plates may be dried at room temperature and stored at 4° C. for up to four months.

4. Sample Collection

All samples may be taken from female subjects by physicians or physician assistants during visits for gynecological examinations. Cotton swabs may be used to gather endocervical cells. Cells for the ThinPrep Pap smear (Cytyc Corporation, Stamford, Conn.) may be dispersed in ThinPrep preservative solution. Cells for the HPV DNA Hybrid Capture assay (Digene Corporation, Silver Spring, Md.) may be suspended in the same medium. Both the ThinPrep Pap smear and the HPV DNA Hybrid Capture assay are further elucidated below.

Venous blood may be obtained by prescribed phlebotomy methods, with a 21- or 22-gauge double-pointed needle into a "red top" tube. A total of 7-9 mL blood may be taken from each subject. After allowing 15-20 minutes at room temperature for clot formation, the blood may be centrifuged at 2,500 g for 15 minutes. Serum may be separated by aspiration from the clotted cells, using a disposable pipette, dispensed into Eppendorf tubes as 0.25-ml aliquots, for storage at −80° C.

5. Immunoassay

For negative samples, serum may be obtained from virgin females, ages 14 and 15, and from adult sexually active, monogamous women, more than 25 years old, with histories of no Pap smear abnormalities and DNA verification of HPV absence. Positive samples consisted of serum obtained from females diagnosed with cervical cancer or precancerous disease. Subject and control sera may be diluted 1:25 with wash buffer (0.1% bovine serum albumin and 0.5% Tween-20 in phosphate buffered saline, pH 7.0). To each well, 100 µL of diluted serum may be added, and the assay plate incubated for one hour at room temperature with shaking. Each well may then be rinsed three times, each with 200 µL wash buffer. Each rinse may be for five minutes. The plate may be emptied each time by tapping residual liquid onto a clean paper towel.

To each well may be added 100 µL horseradish peroxidase conjugated-mouse-anti-human IgG diluted 1:12,000 with wash buffer. The assay plate may then be incubated for 1 hour at room temperature. Using multiple pipettes, each well may be rinsed with 200 µL wash buffer four times. Each rinse may be for five minutes. Before each rinse, the plate may be emptied and residual liquid tapped on a paper towel.

To each well may be added 100 µL 3,3',5,5' tetramethylbenzidine, a substrate for horseradish peroxidase. This may be incubated at room temperature until a visually obvious green-blue color develops, typically within 10-15 minutes, and the reaction stopped by placing 150 µL 1.5 M sulphuric acid ($H_2SO_4$) into each well.

6. Comparisonal Tests—ThinPrep Pap Test and HPV DNA Hybrid Capture

ThinPrep Pap Test—The ThinPrep Pap test Pap smears may be used for cytological verification of the presence or absence of cellular abnormalities indicative of cancer or precancer. Allowed by the US Food and Drug Administration as a replacement for the conventional Pap smear, the ThinPrep Pap Test overcomes the limitations of the conventional method. By improving the way the sample slide is prepared, the ThinPrep Pap Test may actually improve the quality of the test. In clinical trials, the ThinPrep Pap Test improved the detection of low-grade and more severe lesions by 65% in screening populations and by 6% in high-risk populations. Its use also reduced the number of less-than-adequate specimens by more than 50%.

Rather than smearing the cervical sample onto a slide as is done with the conventional Pap smear, the cervical swab may be rinsed in a vial of preserving solution. The specimen may be sent to a certified clinical laboratory, where an instrument, the ThinPrep 2000 processor, may be used to disperse and filter the contents to reduce blood, mucus, and inflammation. A thin, even layer of the cervical cells may then be mechanically deposited onto a slide, the result being a uniform preparation of well-preserved cells ready for precise microscopic examination. Slides may be microscopically examined and interpreted by a board certified gynecological cytologist.

Hybrid Capture II HPV DNA Testing—The Hybrid Capture II HPV DNA test (Digene Corporation, Silver Springs, Md.) may be employed as a comparison to ELISA tests employing peptides of the invention. It is approved by the U.S. Food and Drug Administration to test for oncogenic HPV DNA, as reflexive follow-up of a Atypical Squamous Cells of Undetermined Significance (ASCUS) or other abnormal Pap results. Indeed, the Hybrid Capture II HPV DNA test discerns virus DNA and not cervical disease, but all precancerous and cancerous states include HPV DNA presence. The hybrid capture involves a molecular hybridization that uses non radioactive probes with amplification of the detection of the hybrid ones for chemoluminescence. The material for analysis may be denatured and reacts with specific genic probe forming hybrid RNA/DNA that are captured by antibodies that cover the walls of the tube. To follow the hybrids immobilized, these may be reacted with specific antibodies against RNA/DNA conjugated with alkaline phosphatase. Forming a stable substratum, the nucleic acid hybrids may be detected by chemoluminescence via spectometry.

The test may be run according to the manufacturer's protocol using the microtiter plate based format and probes for "high carcinogenic risk" or "oncogenic" HPV types. Human papillomavirus determinations may be quantitative, with samples producing readings of 1 or more times the positive control (1 pg/mL HPV DNA or 5000 HPV genome copies per test) considered to contain virus DNA.

7. Visualization/Interpretation of Completed ELISA Tests

Presence of an antibody-peptide complex may be signaled by visualizing physical-chemical changes that occur upon formation of an antibody-peptide complex. Physical-chemical changes may occur in connection with oxidation reactions and other chemical reactions. Physical-chemical reactions may be detecting using a spectrophotometer or the like.

The bottom of the titer plate may be cleaned with 70% ethanol, and the titer plate loaded into the spectrophotometer. Absorbance may be read at 450 nm, with 100 mL of TMB solution plus 100 mL of 2N HCl used as a blank control.

8. Results

The results comparing Pap smear cytology, Digene HPV DNA assays, and immunoassay according to the invention are shown in FIGS. 1 and 2. Referring now to FIGS. 1 and 2, sixteen female subjects were tested. Samples from women with a low pre-test probability by virtue of sexual history and/or Pap smear history were negative in all samples for all tests actually performed, evidenced by absorbance values that averaged 0.19 compared against the 0.42 average for subjects with varied states of disease, with the singular exception discussed below. This indicates a low rate of false positives and a high negative predictive value.

Samples from subjects with a low pre-test probability by virtue of sexual history and/or Pap smear history mostly had lower absorbance values, as stated above. However, Subject 6 was exceptional in terms of its higher values for HPV E2 antibody-antigen complexes, averaging 0.42 with 0.44 for SEQ ID NO 1, 0.32 for SEQ ID NO 2 and 0.49 for SEQ ID NO 3. Subject 6 otherwise yielded absorbance values that averaged 0.21. These data are not indicators of infection or dysplasia. With no HPV DNA detected in Subject 6, it is more likely that these elevated HPV E2 absorbance values were vestiges of a previous but now cleared HPV infection.

Samples from women with a high pre-test probability by virtue of proven clinical/pathological history largely showed immunoassays performed according to the invention as positive, indicated by higher absorbance values. Average absorbance values were 0.42 for serum from diseased Subjects 8-16, and 0.47 with consideration of only those peptides derived from the E6 and E7 oncoproteins. Furthermore, these values are significantly higher on average than absorbance values from non-diseased or healthy subjects ($p<0.001$). These results point to a high positive predictive value. Since in some cases one or more assays yielded somewhat lower absorbance values, the merit to employing combinations of peptides is demonstrated. The low false positives and high true positives indicates a test of high sensitivity and high specificity for precancerous disease and cancers.

Of central importance is that Subjects 15 and 16 had pathology proven adenocarcinoma of the cervix, that Subjects 13 and 14 had pathology proven squamous cell carcinoma of the cervix, and that serum from these subjects were characterized by higher absorbance values. It is likewise important that Pap smear scrutiny for Subject 15 resulted in no findings of cell abnormalities in the face of significant cervical disease. That Pap smear cytology can miss adenocarcinomas underscores the usefulness of the peptides of the present invention.

It is likewise notable that serum from Subject 7 showed lower absorbencies for virtually all peptides of the present invention when compared against results for Subjects 8-16. Although Subject 6 came with a pathology proven diagnosis of cell abnormalities, immunoassays using peptides of the invention were more in accord with the negative DNA results. These data were considered to indicate cell abnormalities having nothing to do with oncogenic virus and a consequent small likelihood of future disease progression to a more serious dysplasia or cancer. These results point out the further utility of the present invention as described herein.

From the above discussion, it will be appreciated that the present invention provides novel antibody reactive protein sequences or peptides isolated from HPV 16 and 18 E2, E6 and E7 early coding regions. In preferred design, the novel protein sequences or peptides provide a marker for a simple, rapid, less expensive, more sensitive and more specific test for detecting or diagnosing not only HPV infections, but also most, if not all HPV associated cellular abnormalities, pre-cancerous cells, cancers and neoplasms.

Unlike the prior art, the present invention provides methodologies for detecting or diagnosing cancer or cellular abnormalities by obtaining a body tissue sample, reacting the sample with a novel protein sequences or peptides isolated from HPV 16 and 18 E2, E6 and E7 early coding regions to form an antibody-peptide complex; and detecting the antibody-peptide complex.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

The invention claimed is:

1. A method for detecting or diagnosing cancer or cellular abnormalities, said method comprising the steps of:
   reacting a sample of body fluid or tissue likely to contain antibodies with a protein sequence or peptide isolated from the E7 early coding region of human papillomavirus (HPV) 16 as set forth in SEQ. ID. NO.: 6;
   forming an antibody-peptide complex comprising the isolated protein sequence or peptide and said sample antibodies; and
   detecting said antibody-peptide complex, wherein detecting the antibody-peptide complex indicates cancer or cellular abnormality, wherein said cellular abnormalities are selected from the group consisting of dysplasias, koilocytosis, hyperkeratosis, precancerous conditions, intraepithelial neoplasias, intraepithelial lesions, high-grade dysplasias, invasive cancers, malignant cancers, premalignant cells, and precancerous cells.

2. The method for detecting or diagnosing cancer or cellular abnormalities as defined in claim 1, wherein said isolated protein sequence or peptide comprises one or more additional glycine residues added at a carboxyl terminal residue of said isolated protein sequence or peptide.

3. The method for detecting or diagnosing cancer or cellular abnormalities as defined in claim 1, wherein said isolated protein sequence or peptide comprises one or more additional asparagine residues added at a carboxyl terminal residue of said isolated protein sequence or peptide.

4. The method for detecting or diagnosing cancer or cellular abnormalities as defined in claim 1, wherein said isolated protein sequence or peptide comprises a combination of glycine and asparagine residues added at a carboxyl terminal residue of said isolated protein sequence of peptide.

5. The method for detecting or diagnosing cancer or cellular abnormalities as defined in claim 1, wherein said cysteine residues of said isolated protein sequence or peptide is substituted with a carboxymethlycysteine residue.

6. The method for detecting or diagnosing cancer or cellular abnormalities as defined in claim 1, wherein said diagnostic method is directed to detecting or diagnosing an HPV epitope.

7. The method for detecting or diagnosing cancer or cellular abnormalities as defined in claim 1, wherein said HPV epitope is an antigenic region against which antibody reactivity would occur.

8. The method for detecting or diagnosing cancer or cellular abnormalities as defined in claim 1, wherein said diagnostic meted is directed to detecting or diagnosing an HPV associated cell abnormality.

9. The method for detecting or diagnosing cancer or cellular abnormalities as defined in claim 1, wherein said diagnostic method is directed to detecting or diagnosing an HPV associated precancerous or premalignant condition.

10. The method for detecting or diagnosing cancer or cellular abnormalities as defined in claim 1, wherein said diagnostic method is directed to detecting or diagnosing an HPV associated cancer.

11. The method for detecting or diagnosing cancer or cellular abnormalities as defined in claim 1, wherein said diagnostic method is directed to detecting or diagnosing cervical dysplasia.

12. The method for detecting or diagnosing cancer or cellular abnormalities as defined in claim 1, wherein said diagnostic method is directed to detecting or diagnosing cervical carcinoma.

13. The method for detecting or diagnosing cancer or cellular abnormalities as defined in claim 1, wherein said diagnostic method is directed to detecting or diagnosing cervical cellular abnormalities selected from the group consisting of koilocytosis, hyperkeratosis, precancerous conditions encompassing intraepithelial lesions, high-grade dysplasias, invasive cancers and malignant cancers.

14. The method for detecting or diagnosing cancer or cellular abnormalities as defined in claim 1, wherein said diagnostic method is directed to detecting or diagnosing adenocarcinoma of the uterine cervix.

15. The method for detecting or diagnosing cancer or cellular abnormalities as defined in claim 1, wherein said protein sequence or peptide isolated from the E7 early coding region comprises detection or diagnosis of premalignant cell transformation, a precancerous condition or cancer.

16. The method for detecting or diagnosing cancer or cellular abnormalities as defined in claim 1, wherein said detection step further comprises the step of visually inspecting said antibody-peptide complex for a color change.

17. The method for detecting or diagnosing cancer or cellular abnormalities as defined in claim 1, wherein said detection step further comprises inspecting said antibody-peptide complex for physical-chemical changes.

18. The method for detecting or diagnosing cancer or cellular abnormalities as defined in claim 17, wherein said inspection step further comprises inspecting said antibody-peptide complex using a spectrophotometer.

* * * * *

SEQUENCE LISTING

```
<160> NUMBER OF SEQ ID NOS: 8

<210> SEQ ID NO 1
<211> LENGTH: 22
<212> TYPE: PRT
<213> ORGANISM: Artificial Sequence
<220> FEATURE:
<223> OTHER INFORMATION: Derived from the E2 region of HPV 18

<400> SEQUENCE: 1

Lys Gln Leu Gln His Thr Pro Ser Pro Tyr Ser Ser Thr Val Ser Val
1               5                   10                  15

Gly Thr Ala Lys Thr Tyr
            20

<210> SEQ ID NO 2
<211> LENGTH: 17
<212> TYPE: PRT
<213> ORGANISM: Artificial Sequence
<220> FEATURE:
<223> OTHER INFORMATION: Derived from the E2 early coding region of HPV
      16

<400> SEQUENCE: 2

Lys His Gly Tyr Thr Val Gln Phe Asp Gly Ile Cys Asn Thr Met His
1               5                   10                  15

Tyr

<210> SEQ ID NO 3
<211> LENGTH: 23
<212> TYPE: PRT
<213> ORGANISM: Artificial Sequence
<220> FEATURE:
<223> OTHER INFORMATION: Derived from the E2 early coding region of HPV
      16

<400> SEQUENCE: 3

His Ala Gly Gly Gln Val Ile Leu Cys Pro Thr Ser Val Phe Ser Ser
1               5                   10                  15

Asn Glu Val Ser Ser Pro Glu
            20

<210> SEQ ID NO 4
<211> LENGTH: 22
<212> TYPE: PRT
<213> ORGANISM: Artificial Sequence
<220> FEATURE:
```

```
<223> OTHER INFORMATION: Derived from the E6 early coding region of HPV
      16

<400> SEQUENCE: 4

Arg Asp Gly Asn Pro Tyr Ala Val Cys Asp Lys Cys Leu Lys Phe Tyr
1               5                   10                  15

Ser Lys Ile Ser Glu Tyr
            20

<210> SEQ ID NO 5
<211> LENGTH: 22
<212> TYPE: PRT
<213> ORGANISM: Artificial Sequence
<220> FEATURE:
<223> OTHER INFORMATION: Derived from the E6 early coding region of HPV
      18

<400> SEQUENCE: 5

Lys Cys Ile Asp Phe Gly Ser Arg Ile Arg Glu Leu Arg His Tyr Ser
1               5                   10                  15

Asp Ser Val Tyr Gly Asp
            20

<210> SEQ ID NO 6
<211> LENGTH: 21
<212> TYPE: PRT
<213> ORGANISM: Artificial Sequence
<220> FEATURE:
<223> OTHER INFORMATION: Derived from the E7 early coding region of HPV
      16

<400> SEQUENCE: 6

Glu Gln Leu Asn Asp Ser Ser Glu Glu Glu Asp Glu Ile Asp Gly Pro
1               5                   10                  15

Ala Gly Gln Ala Glu
            20

<210> SEQ ID NO 7
<211> LENGTH: 21
<212> TYPE: PRT
<213> ORGANISM: Artificial Sequence
<220> FEATURE:
<223> OTHER INFORMATION: Derived from the E7 early coding region of HPV
      16

<400> SEQUENCE: 7

Glu Thr Thr Asp Leu Tyr Cys Tyr Glu Gln Leu Asn Asp Ser Ser Ser
1               5                   10                  15

Glu Asp Glu Ile Asp
            20

<210> SEQ ID NO 8
<211> LENGTH: 22
<212> TYPE: PRT
<213> ORGANISM: Artificial Sequence
<220> FEATURE:
<223> OTHER INFORMATION: Derived from the E7 early coding region of HPV
      18

<400> SEQUENCE: 8

His Leu Gln Pro Gln Asn Glu Ile Pro Val Asp Leu Leu Cys His Glu
1               5                   10                  15

Gln Leu Ser Asp Ser Glu
            20
```